United States Patent [19]
Hioki et al.

[11] Patent Number: 6,066,674
[45] Date of Patent: *May 23, 2000

[54] GERMICIDAL-DISINFECTANT DETERGENT COMPOSITION

[75] Inventors: Yuichi Hioki; Tadashi Moriyama; Chikako Matsumoto; Juri Sata; Yoshinori Tamura, all of Wakayama, Japan

[73] Assignee: Kao Corporation, Tokyo, Japan

[ * ] Notice: This patent is subject to a terminal disclaimer.

[21] Appl. No.: 08/994,009

[22] Filed: Dec. 18, 1997

Related U.S. Application Data

[62] Division of application No. 08/925,651, Sep. 9, 1997, Pat. No. 5,739,168, which is a continuation of application No. 08/594,389, Jan. 31, 1996, abandoned, which is a continuation of application No. 08/291,082, Aug. 18, 1994, abandoned.

[30] Foreign Application Priority Data

Aug. 19, 1993 [JP] Japan ................................ 5-205076
Aug. 19, 1993 [JP] Japan ................................ 5-205077

[51] Int. Cl.⁷ .......................... A01N 25/22; A01N 25/30; A01N 33/12
[52] U.S. Cl. ............................. 514/643; 514/642
[58] Field of Search ..................... 514/642, 643, 514/836; 564/233

[56] References Cited

U.S. PATENT DOCUMENTS

| | | | |
|---|---|---|---|
| 4,134,971 | 1/1979 | Inoue et al. | 424/601 |
| 4,263,276 | 4/1981 | Harvey | 424/52 |
| 4,305,928 | 12/1981 | Harvey | 424/52 |
| 4,335,102 | 6/1982 | Nakashima et al. | 424/52 |
| 4,704,222 | 11/1987 | Smith | 510/396 |
| 4,714,563 | 12/1987 | Kajs et al. | 252/107 |
| 5,296,215 | 3/1994 | Burke et al. | 424/49 |
| 5,405,604 | 4/1995 | Hall | 424/54 |
| 5,439,681 | 8/1995 | Khan et al. | 424/400 |
| 5,858,936 | 1/1999 | Tamura et al. | 510/131 |
| 5,908,856 | 6/1999 | Oldenhove | 514/399 |
| 5,922,693 | 7/1999 | Oldenhove | 514/63 |

FOREIGN PATENT DOCUMENTS 10183173  7/1998  Japan .

*Primary Examiner*—Robert H. Harrison
*Attorney, Agent, or Firm*—Oblon, Spivak, McClelland, Maier & Neustadt, P.C.

[57] ABSTRACT

A germicidal-disinfectant detergent composition comprising (a) a cationic germicide, (b) a metal chelating agent and (c) at least one surfactant selected from anionic surfactants, nonionic surfactants and amphoteric surfactants is described. Excellent detergency and germicidal action are provided.

10 Claims, No Drawings

GERMICIDAL-DISINFECTANT DETERGENT COMPOSITION

This application is a Division of application Ser. No. 08/925,651, filed Sep. 9, 1997 U.S. Pat. No. 5,739,168, allowed, which is a Continuation of application Ser. No. 08/594,389, filed Jan. 31, 1996 abandoned, which is a Continuation of application Ser. No. 08/291,082, filed Aug. 18, 1994 abandoned.

BACKGROUND OF THE INVENTION

1. Field of the Invention

The present invention relates to a germicidal-disinfectant detergent composition comprising a cationic germicide which provides sustained, high level antibacterial activity, excellent germicidal-disinfectant action, and excellent detergent action.

2. Description of the Background Art

Cationic germicides generally have both a broad antibacterial spectrum and immediate effects, and are thus widely used in hospitals, etc. Germicidal-disinfectant detergents comprising a cationic germicide and a surfactant are known. However, such detergents suffer from the fact that anionic surfactants and other substances having a negative charge, such as proteins, when present greatly lower the activity of the cationic germicide.

Prior art attempts at preventing this reduction in germicidal activity having included coating the cationic germicide with a high molecular weight nonionic surfactant or a pH-sensitive polymer, and adding the cationic germicide in excess. Unfortunately, the coating processes reduce the activity of the cationic germicide and the process making use of excess germicide is not preferable from an economic point of view.

SUMMARY OF THE INVENTION

It is an object of the present invention to provide a germicidal-disinfectant detergent composition in which the antibacterial activity of a cationic germicide contained therein is not lowered, even in the presence of a substance having a negative charge. Providing a germicidal-disinfectant composition having excellent detergency is also an object of the present invention.

The present inventors have discovered that when a metal chelating agent is used in combination with a composition obtained by mixing a cationic germicide and at least one of an anionic surfactant, a nonionic surfactant and/or an amphoteric surfactant, a germicidal disinfectant detergent composition is obtained wherein the cationic germicide exhibits its inherent action without a lowering of its antibacterial activity even when anionic surfactants and/or negative-charge carrying species are present. Moreover, excellent detergency is provided, thus leading to completion of the present invention.

In one embodiment of the present invention, there is provided a germicidal-disinfectant detergent composition comprising (a) a cationic germicide, (b) a metal chelating agent, preferably present in an amount of at least 0.5 mol per mol of the germicide and (c) at least one surfactant selected from the group consisting of anionic surfactants, nonionic surfactants and amphoteric surfactants.

In another embodiment of the present invention, there is provided a method for germicidal and disinfectant cleaning, which comprises cleaning a contaminated substance with a composition comprising (a) a cationic germicide, (b) a metal chelating agent, preferably present in an amount of at least 0.5 mol per mol of the germicide and (c) at least one surfactant selected from the group consisting of anionic surfactants, nonionic surfactants and amphoteric surfactants.

The germicidal-disinfectant detergent composition of the present invention provides excellent antibacterial, antigermicidal, antiviral, etc. activity (hereinafter referred to as germicidal action or effect), wherein the action of the cationic germicide is not lowered even in the presence of a substance having a negative charge, such as an anionic surfactant. The composition of the present invention is also excellent in its detergency. Therefore, the use of the germicidal-disinfectant detergent composition according to the present invention in the cleansing of the skin, etc. can bring about a greatly increased germicidal effect compared with conventional germicides.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

Components (a), (b) and (c) according to the invention germicidal-disinfectant composition and method are described below.

Examples of the component (a) cationic germicides useful in the practice of the present invention include cationic surfactant-type germicides such as benzethonium chloride, benzalkonium chloride, dialkyldimethylammonium halides, monoalkyltrimethylammonium halides and their variants having the counter ions thereof changed to other anions; biguanide type germicides such as chlorhexidine and chlorhexidine gluconate; amino acid surfactants such as alkyldiamino ethylglycines and alkylpolyamino ethylglycines; and the like. The cationic germicides carry a positive charge and are typically ion-paired with a counter anion so as to provide a neutral salt when in the solid phase. Other useful cationic germicides are described in the *The Merck Index*, Merck & Co., Inc., Rahway, N.J., 1989 incorporated herein by reference. Mixtures of cationic germicides can be used. The cationic germicides are preferably incorporated in the invention composition in an amount of 0.1–10 wt. % (hereinafter indicated merely by "%"), particularly 0.5–5% based on the total weight of the composition.

No particular limitation is imposed on the component (b) metal chelating agent other than its functional capacity to chelate a metal ion. Examples of such chelating agents useful in the present invention include ethylenediaminetetraacetic acid, hydroxyethyl-ethylenediaminetriacetic acid, diethylenetriamine pentaacetic acid, nitrilotriacetic acid, triethylenetetramine hexaacetic acid, phosphonic acids, tripolyphosphoric acid, ethylene glycol-bis(2-aminoethyl ether)tetraacetic acid, citric acid, maleic acid, polyacrylic acid, isoamylene-maleic acid copolymers, silicic acid, gluconic acid, hydroxybenzylimidinoaceticacid, imidinoacetic acid and salts thereof. Of these, ethylenediaminetetraacetic acid, hydroxyethylethylenediaminetriacetic acid, citric acid, tripolyphosphoric acid and salts thereof are particularly preferred. Mixtures can be used.

It is preferred that the metal chelating agent be present in an amount of at least 0.5 mol per mol of the cationic germicide (a). Generally, it is preferably incorporated in a proportion of 0.5–5 mol, more preferably 0.5–2 mol, most preferably 1–2 mol per mol of the germicide. If the proportion is lower than 0.5 mol, the effect of preventing the lowering of the antibacterial activity of the germicide in the presence of a negative charge is not fully achieved. The metal chelating agent is preferably incorporated in the invention composition in a proportion of 0.05–5%, particularly 0.2–3% based on the total weight of the composition.

In certain shampoos and rinses, a chelating agent may be incorporated in addition to an anionic surfactant and a cationic surfactant. In such cases, however, the amount of chelating agent incorporated is extremely small, and even if a germicide was present, the antibacterial activity of the germicide would not be protected from being reduced, unlike the case of the present invention.

Examples of the component (c) anionic surfactants useful in the present invention include salts of higher fatty acids preferably having 10–14 carbon atoms, salts of higher alcohol sulfates preferably having 10–18 carbon atoms, salts of higher alcohol sulfonic acids preferably having 10–18 carbon atoms, salts of sulfated fatty acids preferably having 10–18 carbon atoms, salts of sulfonated fatty acids preferably having 10–18 carbon atoms, salts of higher alcohol phosphates the alcohol moiety of which preferably has 10–14 carbon atoms, salts of fatty acid ester sulfates preferably having 10–18 carbon atoms, salts of fatty acid ester sulfonates preferably having 10–18 carbon atoms, salts of higher alcohol ether sulfates preferably having 10–18 carbon atoms, salts of higher alcohol ether sulfonates preferably having 10–18 carbon atoms, salts of higher alcohol ether substituted acetic acids the alcohol moiety of which preferably has 8–18 carbon atoms (number of mols of ethylene oxide added: 1–15), condensates of a fatty acid and an amino acid, salts of fatty acid amide alkylolated sulfates preferably having 10–18 carbon atoms, salts of fatty acid amide alkylated sulfonic acids preferably having 10–18 carbon atoms, salts of carboxymethyl-substituted ethoxylated fatty acid amides the acyl moiety of which preferably has 8–18 carbon atoms (number of mols of ethylene oxide added: 1–15), salts of sulfosuccinates, alkylbenzenesulfonates preferably having 8–18 carbon atoms, alkylphenol sulfonates preferably having 8–18 carbon atoms, alkylnaphthalenesulfonates preferably having 8–18 carbon atoms, alkylbenzoimidazolesulfonates preferably having 1–18 carbon atoms, and the like. Preferred salts are the Na, K, TEA (Triethanolamine), $NH_4^+$ salts. Mixtures can be used.

Examples of the component (c) nonionic surfactants useful in the present invention include polyoxyethylene alkyl ethers, polyoxyethylene alkylene ethers, polyoxyethylene sorbitan fatty acid esters, polyoxyethylene sorbite fatty acid esters, alkyl polyglycosides preferably having 8–18 carbon atoms, sucrose fatty acid esters preferably having 8–18 carbon atoms, alkyl polyglycerol ethers, and the like. Mixtures can be used.

Examples of the component (c) amphoteric surfactants useful in the present invention include alkyldimethylamino fatty acid betaines preferably having 8–18 carbon atoms, alkyldimethylamine oxides preferably having 8–18 carbon atoms, alkylcarboxymethylhydroxyethylimidazolium betaines preferably having 8–18 carbon atoms, and the like. Mixtures can be used.

Of these, an anionic surfactant alone (meaning one or a mixture thereof) or a combination of an anionic surfactant (one or a mixture) with a nonionic surfactant (one or a mixture) and/or an amphoteric surfactant (one or a mixture) is preferred as component (c).

Of these surfactants, the salts of higher fatty acids, the salts of higher alcohol phosphates, the salts of higher alcohol ether-substituted acetic acids, salts of carboxymethyl-substituted ethoxylated fatty acid amides, the alkyl polyglycosides, the alkyldimethylamino fatty acid betaines and the alkyldimethylamine oxides are particularly preferred. The Na, K, TEA (Triethanolamine), $NH_4^+$ salts are preferred. To the extent that there is any overlap between components (a) and (c), component (c) is at least one surfactant different from the material described in component (a) selected from the group consisting of anionic surfactants, nonionic surfactants, amphoteric surfactants and mixtures thereof.

In order to provide the desired detergent effect, component (c), preferably an anionic surfactant alone or a combination of an anionic surfactant with a nonionic surfactant and/or an amphoteric surfactant, is preferably incorporated in the invention composition in an amount of 1–80%, particularly 5–50% based on the total weight of the composition. When mixtures of anionic and nonionic surfactants are used, the anionic surfactant is preferably present in from 1 to 70%, and the nonionic surfactant is present in from 1 to 70% based on the total wt % of the component (c) surfactant. When anionic, nonionic and amphoteric surfactants are all present, the preferred amounts are 1 to 70, 1 to 70, and 1 to 70, respectively based on the total wt % of the component (c) surfactant.

In the germicidal-disinfectant detergent composition according to the present invention, the antibacterial, antiviral, etc. activity of the cationic germicide is not at all, or not significantly reduced even in the presence of a substance having a negative charge, such as an anionic surfactant, because the cationic germicide is present in combination with a metal chelating agent. Therefore, it is also possible to incorporate an additional anionic polymer and/or the like into the germicidal-disinfectant detergent composition of the present invention. Examples of such anionic polymers include polymers having carboxyl groups, sulfonyl groups, sulfate residues or the like, for example, salts of poly(meth)acrylic acid, salts of polyvinyl alcohol sulfate, naphthalenesulfonic acid-formalin condensates or alkylene oxide adducts thereof.

In the germicidal-disinfectant detergent composition according to the present invention other additives, for example, salts, viscosity builders, germicides other than those described above, viscosity depressants, solvents such as ethanol and propylene glycol, perfume bases, colorants, etc. may be suitably incorporated within conventional limits not impeding the effects of the present invention, as needed.

The germicidal-disinfectant detergent composition according to the present invention can be prepared by any method known per se in the art; for example, by mixing and/or stirring the individual components, and may be provided in various forms such as aqueous solution, solid, aqueous suspension, and the like.

The germicidal-disinfectant detergent composition according to the present invention can be applied to surfaces, etc. with the object of germicidal and disinfectant cleaning; for example, handwashes, face cleansers, body shampoos, hair shampoos, laundry detergents and instrument-cleaning detergents in fields associated with medical care, food and environmental sanitation.

While not wishing to be bound by a particular theory, the present inventors believe a clue to the theory of operation of the invention is discernable from the $^{13}$C-NMR chemical shift of the α-carbon of a fatty acid salt (which is an example of a present invention anionic surfactant): it is shifted to higher magnetic field in the presence of a cationic germicide. Therefore, it is believed that these substances undergo some interaction with each other. When EDTA (which is an example of a present invention metal chelating agent) is present in or added to the above mixture, the $^{13}$C-NMR chemical shift of the α-carbon is returned to a lower magnetic field. It is therefore considered that the addition of the metal chelating agent prevents the reduction of the germicidal activity of the cationic germicide by eliminating or reducing the association of the metal chelating agent with the cationic germicide, and the like, so that the cationic germicide is returned to its original uninhibited state, thereby allowing its inherent action to be exhibited.

The present invention will hereinafter be described in detail by the following examples. However, it should be borne in mind that this invention is not limited to or by these examples.

EXAMPLE 1

The germicidal effects of various germicides (benzalkonium hexadecylphosphate, benzalkonium chloride, didecyl-dimethylammonium chloride and chlorhexidine gluconate) both in the presence of an anionic surfactant and in the presence of a metal chelating agent added to a mixture of germicide and anionic surfactant were investigated.

Method

Triethanolamine laureate was used as the anionic surfactant and was mixed in a proportion of 28.35 parts by weight with 1 part by weight of each of the various germicides listed above, and to portions of the resultant mixtures was separately added sodium EDTA as the metal chelating agent in varied proportions of from 0.5–10.0 mols per mol of the germicide. Sterilized distilled water was added to each of the resulting mixtures to provide compositions having 100 parts by weight in total. As controls, systems to which the metal chelating agent, triethanolamine laureate or germicide was not added, and individual systems of these components, were prepared.

A germicidal test was performed in the following manner. Diluted systems of each mixture described above were prepared to inoculate each of germs (*Escherichia coli* IFO 3972 and *Pseudomonas aeruginosa* IFO 12689) to be tested to determine the concentration of the germicide at which the germs were completely killed, and the time required to completely kill the germs. More specifically, 0.1 ml of an SCD medium (product of Nippon Seiyaku K. K.) containing precultured germs (about $10^9$–$10^{10}$ cells/ml) was taken out and inoculated in 10 ml of the systems described above diluted to predetermined concentrations (germicide concentration: 1, 5, 10, 25, 50, 75, 100, 200, 300 or 500 ppm) to conduct the test at room temperature. When predetermined periods of time (5, 10, 15 and 30 minutes) elapsed a portion of the system inoculated with the germs was taken out with a platinum loop and inoculated in a micro Petri dish (96-cell wells, product of CORNING Co.) containing 0.3 ml of an SCD medium for after culture. Culture was conducted for 3 days at 30° C. to determine the growth of germs (observation by the naked eye). Among these micro Petri dishes, the number of dishes where germs have been completely killed are defined as the number of sterilized areas (40 areas in the maximum number). The judgement of the efficacy of the tested solution was made by counting the sterilized areas.

The results are shown in Tables 1 and 2.

TABLE 1

| Germicide | Amount added (part by weight) | Amount of triethanolamine laureate added (part by weight) | Amount of chelating agent added (mol) | Effect on *E. coli* (number of sterilized areas) | Effect on *P. aeruginosa* (number of sterilized areas) |
|---|---|---|---|---|---|
| Benzalkonium hexadecylphosphate | 1.0 | 28.35 | 0.5 | 35 | 33 |
| | 1.0 | 28.35 | 1.0 | 35 | 34 |
| | 1.0 | 28.35 | 2.0 | 35 | 34 |
| | 1.0 | 28.35 | 5.0 | 35 | 33 |
| | 1.0 | 28.35 | 10.0 | 35 | 33 |
| | 1.0 | 28.35 | 0 | 2 | 1 |
| | 1.0 | 0 | 1.0 | 35 | 34 |
| | 1.0 | 0 | 0 | 34 | 34 |
| | 0 | 28.35 | 1.0 | 2 | 1 |
| | 0 | 28.35 | 0 | 2 | 1 |
| Benzalkonium chloride | 1.0 | 28.35 | 0.5 | 35 | 34 |
| | 1.0 | 28.35 | 1.0 | 36 | 34 |
| | 1.0 | 28.35 | 2.0 | 36 | 35 |
| | 1.0 | 28.35 | 5.0 | 35 | 35 |
| | 1.0 | 28.35 | 10.0 | 34 | 34 |
| | 1.0 | 28.35 | 0 | 2 | 1 |
| | 1.0 | 0 | 1.0 | 36 | 34 |

TABLE 1-continued

| Germicide | Amount added (part by weight) | Amount of triethanolamine laureate added (part by weight) | Amount of chelating agent added (mol) | Effect on E. coli (number of sterilized areas) | Effect on P. aeruginosa (number of sterilized areas) |
|---|---|---|---|---|---|
| | 1.0 | 0 | 0 | 34 | 33 |
| | 0 | 28.35 | 1.0 | 1 | 1 |
| | 0 | 28.35 | 0 | 0 | 1 |

TABLE 2

| Germicide | Amount added (part by weight) | Amount of triethanolamine laureate added (part by weight) | Amount of chelating agent added (mol) | Effect on E. coli (number of sterilized areas) | Effect on P. aeruginosa (number of sterilized areas) |
|---|---|---|---|---|---|
| Didecyldimethyl-ammonium chloride | 1.0 | 28.35 | 0.5 | 37 | 36 |
| | 1.0 | 28.35 | 1.0 | 38 | 37 |
| | 1.0 | 28.35 | 2.0 | 38 | 37 |
| | 1.0 | 28.35 | 5.0 | 39 | 37 |
| | 1.0 | 28.35 | 10.0 | 36 | 35 |
| | 1.0 | 28.35 | 0 | 3 | 2 |
| | 1.0 | 0 | 1.0 | 37 | 34 |
| | 1.0 | 0 | 0 | 38 | 36 |
| | 0 | 28.35 | 1.0 | 1 | 1 |
| | 0 | 28.35 | 0 | 1 | 0 |
| Chlorhexidine gluconate | 1.0 | 28.35 | 0.5 | 38 | 30 |
| | 1.0 | 28.35 | 1.0 | 32 | 31 |
| | 1.0 | 28.35 | 2.0 | 32 | 31 |
| | 1.0 | 28.35 | 5.0 | 31 | 31 |
| | 1.0 | 28.35 | 10.0 | 30 | 30 |
| | 1.0 | 28.35 | 0 | 2 | 1 |
| | 1.0 | 0 | 1.0 | 34 | 32 |
| | 1.0 | 0 | 0 | 33 | 31 |
| | 0 | 28.35 | 1.0 | 1 | 1 |
| | 0 | 28.35 | 0 | 0 | 1 |

As apparent from Tables 1 and 2, it was confirmed that the germicidal action of the cationic germicides is markedly hindered by the addition of the anionic surfactant, but is recovered by adding, to these systems, a metal chelating agent in a proportion of 0.5–10 mol per mol of the cationic germicide.

EXAMPLE 2

Germicidal effects of various germicides (benzalkonium hexadecylphosphate and benzalkonium chloride) both in the presence of an anionic surfactant (triethanolamine laureate) and in the case where sodium citrate or sodium tripolyphosphate (metal chelating agents) was added to such a mixture were investigated. A germicidal test was performed in the same manner as in Example 1. As a result, and as shown in Tables 3 and 4, the germicidal action of the cationic germicides is markedly hindered by the addition of the anionic surfactant, but is recovered by adding, to these systems, sodium citrate or sodium tripolyphosphate in a proportion of 0.5–10 mols per mol of the cationic germicide.

TABLE 3

| Germicide | Amount added (part by weight) | Amount of triethanolamine laureate added (part by weight) | Amount of sodium citrate added (mol) | Effect on E. coli (number of sterilized areas) | Effect on P. aeruginosa (number of sterilized areas) |
|---|---|---|---|---|---|
| Benzalkonium hexadecylphosphate | 1.0 | 28.35 | 0.5 | 31 | 29 |
| | 1.0 | 28.35 | 1.0 | 32 | 29 |
| | 1.0 | 28.35 | 2.0 | 32 | 31 |
| | 1.0 | 28.35 | 5.0 | 31 | 31 |
| | 1.0 | 28.35 | 10.0 | 30 | 28 |
| | 1.0 | 28.35 | 0 | 1 | 1 |
| | 1.0 | 0 | 1.0 | 35 | 34 |
| | 1.0 | 0 | 0 | 35 | 34 |
| Benzalkonium chloride | 1.0 | 28.35 | 0.5 | 32 | 30 |
| | 1.0 | 28.35 | 1.0 | 33 | 31 |
| | 1.0 | 28.35 | 2.0 | 33 | 31 |
| | 1.0 | 28.35 | 5.0 | 34 | 31 |
| | 1.0 | 28.35 | 10.0 | 31 | 30 |

TABLE 3-continued

| Germicide | Amount added (part by weight) | Amount of triethanolamine laureate added (part by weight) | Amount of sodium citrate added (mol) | Effect on *E. coli* (number of sterilized areas) | Effect on *P. aeruginosa* (number of sterilized areas) |
|---|---|---|---|---|---|
| | 1.0 | 28.35 | 0 | 2 | 1 |
| | 1.0 | 0 | 1.0 | 36 | 34 |
| | 1.0 | 0 | 0 | 34 | 33 |

TABLE 4

| Germicide | Amount added (part by weight) | Amount of triethanolamine laureate added (part by weight) | Amount of sodium tripolyphosphate added (mol) | Effect on *E. coli* (number of sterilized areas) | Effect on *P. aeruginosa* (number of sterilized areas) |
|---|---|---|---|---|---|
| Benzalkonium hexadecylphosphate | 1.0 | 28.35 | 0.5 | 29 | 28 |
| | 1.0 | 28.35 | 1.0 | 30 | 29 |
| | 1.0 | 28.35 | 2.0 | 30 | 30 |
| | 1.0 | 28.35 | 5.0 | 31 | 30 |
| | 1.0 | 28.35 | 10.0 | 30 | 29 |
| | 1.0 | 28.35 | 0 | 1 | 1 |
| | 1.0 | 0 | 1.0 | 35 | 34 |
| | 1.0 | 0 | 0 | 35 | 34 |
| Benzalkonium chloride | 1.0 | 28.35 | 0.5 | 30 | 29 |
| | 1.0 | 28.35 | 1.0 | 31 | 29 |
| | 1.0 | 28.35 | 2.0 | 31 | 30 |
| | 1.0 | 28.35 | 5.0 | 31 | 31 |
| | 1.0 | 28.35 | 10.0 | 30 | 30 |
| | 1.0 | 28.35 | 0 | 1 | 1 |
| | 1.0 | 0 | 1.0 | 36 | 34 |
| | 1.0 | 0 | 0 | 34 | 33 |

EXAMPLE 3

Germicidal effects of various germicides (benzalkonium hexadecylphosphate and benzalkonium chloride) both in the presence of an anionic surfactant and in the case where an ethylenediaminetetraacetate (dipotassium or disodium salt) as a metal chelating agent was added to such a mixture were investigated. A germicidal test was performed in the same manner as in Example 1. The results are shown in Tables 5 and 6.

TABLE 5

| Germicide | Amount added (part by weight) | Amount of sodium poly-oxyethylene (3.0) lauryl ether sulfate added (part by weight) | Amount of dipotassium ethylenediaminetetraacetate added (mol) | Effect on *E. coli* (number of sterilized areas) | Effect on *P. aeruginosa* (number of sterilized areas) |
|---|---|---|---|---|---|
| Benzalkonium hexadecylphosphate | 1.0 | 15.0 | 0.5 | 31 | 29 |
| | 1.0 | 15.0 | 1.0 | 33 | 30 |
| | 1.0 | 15.0 | 2.0 | 34 | 31 |
| | 1.0 | 15.0 | 5.0 | 33 | 31 |
| | 1.0 | 15.0 | 10.0 | 33 | 30 |
| | 1.0 | 15.0 | 0 | 3 | 4 |
| Benzalkonium chloride | 1.0 | 15.0 | 0.5 | 30 | 29 |
| | 1.0 | 15.0 | 1.0 | 31 | 30 |
| | 1.0 | 15.0 | 2.0 | 31 | 30 |
| | 1.0 | 15.0 | 5.0 | 30 | 29 |
| | 1.0 | 15.0 | 10.0 | 29 | 27 |
| | 1.0 | 15.0 | 0 | 2 | 1 |

TABLE 6

| Germicide | Amount added (part by weight) | Triethanolamine lauryl phosphate Amount added (part by weight) | Triethanolamine laureate Amount added (part by weight) | Amount of disodium ethylenediaminetetra-acetate added (mol) | Effect on E. coli (number of sterilized areas) | Effect on P. aeruginosa (number of sterilized areas) |
|---|---|---|---|---|---|---|
| Benzalkonium hexa-decylphosphate | 1.0 | 10.0 | 10.0 | 0.5 | 34 | 32 |
|  | 1.0 | 10.0 | 10.0 | 1.0 | 35 | 32 |
|  | 1.0 | 10.0 | 10.0 | 2.0 | 35 | 32 |
|  | 1.0 | 10.0 | 10.0 | 5.0 | 36 | 33 |
|  | 1.0 | 10.0 | 10.0 | 10.0 | 33 | 30 |
|  | 1.0 | 10.0 | 10.0 | 0 | 2 | 1 |
| Benzalkonium chloride | 1.0 | 10.0 | 10.0 | 0.5 | 35 | 31 |
|  | 1.0 | 10.0 | 10.0 | 1.0 | 36 | 31 |
|  | 1.0 | 10.0 | 10.0 | 2.0 | 36 | 32 |
|  | 1.0 | 10.0 | 10.0 | 5.0 | 36 | 30 |
|  | 1.0 | 10.0 | 10.0 | 10.0 | 35 | 30 |
|  | 1.0 | 10.0 | 10.0 | 0 | 2 | 2 |

EXAMPLE 4

The germicidal effects of various germicides (benzalkonium hexadecylphosphate, benzalkonium chloride, didecyldimethylammonium chloride and chlorhexidine gluconate) both in a system in which an anionic surfactant and/or a nonionic surfactant was mixed with each germicide and in the case where a metal chelating agent was added to the mixed systems were investigated.

Method

The alkyl polyglycoside represented by the following formula (a nonionic surfactant) was mixed in a proportion of 10 parts by weight with 1 part by weight of each of the various germicides.

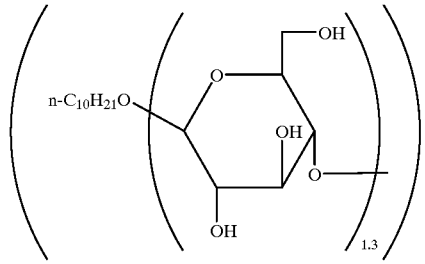

Portions of the resultant mixture were separately mixed with sodium EDTA as the metal chelating agent in varied proportions of 0.5–10.0 mols per mol of the germicide. Sterilized distilled water was added to each of the resulting mixtures to 100 parts by weight in total. As controls, systems to which the metal chelating agent, 3 parts by weight of triethanolamine laureate as the anionic surfactant or germicide was not added, and individual systems of these components, were prepared.

A germicidal test was performed in the following manner. Diluted systems of each mixture were prepared to inoculate each of germs (*Escherichia coli* IFO 3972 and *Pseudomonas aeruginosa* IFO 12689) to be tested in the systems to determine the concentration of the germicide necessary to completely kill the germs, and the time required to do so. More specifically, 0.1 ml of an SCD medium (product of Nippon Seiyaku K. K.) containing precultured germs (about $10^9$–$10^{10}$ cells/ml) was taken out and inoculated in 10 ml of the system diluted to the predetermined concentration (germicide concentration: 1, 5, 10, 25, 50, 75, 100, 200, 300 or 500 ppm) to conduct the test at room temperature. When predetermined periods of time (5, 10, 15 and 30 minutes) went on, a portion of the system inoculated with the germs was taken out by a platinum loop and inoculated in a micro Petri dish (96-cell wells, product of CORNING Co.) containing 0.3 ml of an SCD medium for after culture. Culture was conducted for 3 days at 30° C. to observe the growth of germs (by the naked eye), thereby judging the efficacy by the number of sterilized areas. More specifically, the judgment was made by counting areas (40 areas in the maximum number) where no germ grew on a microplanter.

The results are shown in Tables 7 and 8.

TABLE 7

| Germicide | Amount added (part by weight) | Amount of alkyl polyglycoside added (part by weight) | Amount of triethanolamine laureate added (part by weight) | Amount of chelating agent added (mol) | Effect on E. coli (number of sterilized areas) | Effect on P. aeruginosa (number of sterilized areas) |
|---|---|---|---|---|---|---|
| Didecyldimethylammonium chloride | 1.0 | 10 | 0 | 0.5 | 35 | 32 |
|  | 1.0 | 10 | 0 | 1.0 | 39 | 33 |
|  | 1.0 | 10 | 0 | 2.0 | 39 | 33 |
|  | 1.0 | 10 | 0 | 5.0 | 38 | 32 |
|  | 1.0 | 10 | 3 | 1.0 | 38 | 31 |
|  | 1.0 | 0 | 3 | 1.0 | 36 | 30 |
|  | 1.0 | 10 | 0 | 0 | 30 | 28 |
|  | 1.0 | 10 | 3 | 0 | 1 | 0 |
|  | 0 | 10 | 3 | 1.0 | 0 | 0 |
|  | 0 | 10 | 0 | 0 | 0 | 0 |
| Chlorhexidine gluconate | 1.0 | 10 | 0 | 0.5 | 33 | 31 |

TABLE 7-continued

| Germicide | Amount added (part by weight) | Amount of alkyl polyglycoside added (part by weight) | Amount of triethanolamine laureate added (part by weight) | Amount of chelating agent added (mol) | Effect on E. coli (number of sterilized areas) | Effect on P. aeruginosa (number of sterilized areas) |
|---|---|---|---|---|---|---|
| | 1.0 | 10 | 0 | 1.0 | 35 | 32 |
| | 1.0 | 10 | 0 | 2.0 | 35 | 32 |
| | 1.0 | 10 | 0 | 5.0 | 34 | 32 |
| | 1.0 | 10 | 3 | 1.0 | 34 | 31 |
| | 1.0 | 0 | 3 | 1.0 | 34 | 30 |
| | 1.0 | 10 | 0 | 0 | 29 | 27 |
| | 1.0 | 10 | 3 | 0 | 0 | 0 |
| | 0 | 10 | 3 | 1.0 | 0 | 0 |
| | 0 | 10 | 0 | 0 | 0 | 0 |

TABLE 8

| Germicide | Amount added (part by weight) | Amount of alkyl polyglycoside added (part by weight) | Amount of triethanolamine laureate added (part by weight) | Amount of chelating agent added (mol) | Effect on E. coli (number of sterilized areas) | Effect on P. aeruginosa (number of sterilized areas) |
|---|---|---|---|---|---|---|
| Benzalkonium hexadecylphosphate | 1.0 | 10 | 0 | 0.5 | 33 | 30 |
| | 1.0 | 10 | 0 | 1.0 | 34 | 31 |
| | 1.0 | 10 | 0 | 2.0 | 34 | 31 |
| | 1.0 | 10 | 0 | 5.0 | 34 | 30 |
| | 1.0 | 10 | 3 | 1.0 | 33 | 30 |
| | 1.0 | 0 | 3 | 1.0 | 33 | 30 |
| | 1.0 | 10 | 0 | 0 | 31 | 28 |
| | 1.0 | 10 | 3 | 0 | 1 | 0 |
| | 0 | 10 | 3 | 1.0 | 0 | 0 |
| | 0 | 10 | 0 | 0 | 0 | 0 |
| Benzalkonium chloride | 1.0 | 10 | 0 | 0.5 | 35 | 30 |
| | 1.0 | 10 | 0 | 1.0 | 36 | 31 |
| | 1.0 | 10 | 0 | 2.0 | 37 | 32 |
| | 1.0 | 10 | 0 | 5.0 | 37 | 32 |
| | 1.0 | 10 | 3 | 1.0 | 36 | 32 |
| | 1.0 | 0 | 3 | 1.0 | 35 | 31 |
| | 1.0 | 10 | 0 | 0 | 33 | 29 |
| | 1.0 | 10 | 3 | 0 | 1 | 0 |
| | 0 | 10 | 3 | 1.0 | 0 | 0 |
| | 0 | 10 | 0 | 0 | 0 | 0 |

EXAMPLE 5

The germicidal effects of various germicides (benzalkonium hexadecylphosphate, benzalkonium chloride, didecyldimethylammonium chloride and chlorhexidine gluconate) both in a system in which an anionic surfactant and/or a nonionic surfactant was mixed with each germicide and in a system in which a metal chelating agent was added to the mixtures were investigated.

A germicidal test was performed in the same manner as in Example 4 except that polyoxyethylene (3.0) lauryl ether was used instead of the alkyl polyglycoside as the nonionic surfactant.

The results are shown in Tables 9 and 10.

TABLE 9

| Germicide | Amount added (part by weight) | Amount of polyoxyethylene (3.0) lauryl ether added (part by weight) | Amount of triethanolamine laureate added (part by weight) | Amount of chelating agent added (mol) | Effect on E. coli (number of sterilized areas) | Effect on P. aeruginosa (number of sterilized areas) |
|---|---|---|---|---|---|---|
| Didecyldimethylammonium chloride | 1.0 | 10 | 0 | 0.5 | 36 | 34 |
| | 1.0 | 10 | 0 | 1.0 | 37 | 34 |
| | 1.0 | 10 | 0 | 2.0 | 37 | 35 |
| | 1.0 | 10 | 0 | 5.0 | 38 | 35 |

TABLE 9-continued

| Germicide | Amount added (part by weight) | Amount of poly- oxyethylene (3.0) lauryl ether added (part by weight) | Amount of tri- ethanolamine laureate added (part by weight) | Amount of chelating agent added (mol) | Effect on E. coli (number of sterilized areas | Effect on P. aeruginosa (number of sterilized areas |
|---|---|---|---|---|---|---|
|  | 1.0 | 10 | 3 | 1.0 | 37 | 34 |
|  | 1.0 | 0 | 3 | 1.0 | 37 | 34 |
|  | 1.0 | 10 | 0 | 0 | 30 | 28 |
|  | 1.0 | 10 | 3 | 0 | 1 | 0 |
|  | 0 | 10 | 3 | 1.0 | 0 | 0 |
|  | 0 | 10 | 0 | 0 | 0 | 0 |
| Chlorhexidine gluconate | 1.0 | 10 | 0 | 0.5 | 32 | 30 |
|  | 1.0 | 10 | 0 | 1.0 | 32 | 31 |
|  | 1.0 | 10 | 0 | 2.0 | 33 | 31 |
|  | 1.0 | 10 | 0 | 5.0 | 33 | 31 |
|  | 1.0 | 10 | 3 | 1.0 | 32 | 30 |
|  | 1.0 | 0 | 3 | 1.0 | 32 | 30 |
|  | 1.0 | 10 | 0 | 0 | 29 | 27 |
|  | 1.0 | 10 | 3 | 0 | 1 | 0 |
|  | 0 | 10 | 3 | 1.0 | 0 | 0 |
|  | 0 | 10 | 0 | 0 | 0 | 0 |

TABLE 10

| Germicide | Amount added (part by weight) | Amount of poly- oxyethylene (3.0) lauryl ether added (part by weight) | Amount of tri- ethanolamine laureate added (part by weight) | Amount of chelating agent added (mol) | Effect on E. coli (number of sterilized areas | Effect on P. aeruginosa (number of sterilized areas |
|---|---|---|---|---|---|---|
| Benzalkonium hexa- decylphosphate | 1.0 | 10 | 0 | 0.5 | 34 | 31 |
|  | 1.0 | 10 | 0 | 1.0 | 34 | 31 |
|  | 1.0 | 10 | 0 | 2.0 | 35 | 31 |
|  | 1.0 | 10 | 0 | 5.0 | 35 | 32 |
|  | 1.0 | 10 | 3 | 1.0 | 34 | 31 |
|  | 1.0 | 0 | 3 | 1.0 | 34 | 30 |
|  | 1.0 | 10 | 0 | 0 | 31 | 28 |
|  | 1.0 | 10 | 3 | 0 | 1 | 0 |
|  | 0 | 10 | 3 | 1.0 | 0 | 0 |
|  | 0 | 10 | 0 | 0 | 0 | 0 |
| Benzalkonium chloride | 1.0 | 10 | 0 | 0.5 | 35 | 31 |
|  | 1.0 | 10 | 0 | 1.0 | 36 | 33 |
|  | 1.0 | 10 | 0 | 2.0 | 36 | 33 |
|  | 1.0 | 10 | 0 | 5.0 | 37 | 33 |
|  | 1.0 | 10 | 3 | 1.0 | 35 | 31 |
|  | 1.0 | 0 | 3 | 1.0 | 35 | 31 |
|  | 1.0 | 10 | 0 | 0 | 33 | 29 |
|  | 1.0 | 10 | 3 | 0 | 1 | 0 |
|  | 0 | 10 | 3 | 1.0 | 0 | 0 |
|  | 0 | 10 | 0 | 0 | 0 | 0 |

EXAMPLE 6

The germicidal effects of various germicides (benzalkonium chloride and chlorhexidine gluconate) both in a system in which an anionic surfactant and/or an amphoteric surfactant was mixed with each germicide and in a system in which a metal chelating agent was added to such a system were investigated.

A germicidal test was performed in the same manner as in Example 4 except that alkyldimethylamine oxide represented by the following formula was used as the amphoteric surfactant instead of the alkyl polyglycoside as the nonionic surfactant.

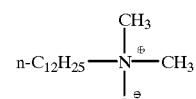

The results are shown in Table 11.

TABLE 11

| Germicide | Amount added (part by weight) | Amount of alkyl-dimethylamine oxide added (part by weight) | Amount of tri-ethanolamine laureate added (part by weight) | Amount of chelating agent added (mol) | Effect on E. coli (number of sterilized areas) | Effect on P. aeruginosa (number of sterilized areas) |
|---|---|---|---|---|---|---|
| Benzalkonium chloride | 1.0 | 10 | 0 | 0.5 | 35 | 31 |
|  | 1.0 | 10 | 0 | 1.0 | 35 | 31 |
|  | 1.0 | 10 | 0 | 2.0 | 36 | 31 |
|  | 1.0 | 10 | 0 | 5.0 | 36 | 32 |
|  | 1.0 | 10 | 3 | 1.0 | 37 | 31 |
|  | 1.0 | 0 | 3 | 1.0 | 35 | 31 |
|  | 1.0 | 10 | 0 | 0 | 30 | 27 |
|  | 1.0 | 10 | 3 | 0 | 0 | 0 |
|  | 0 | 10 | 3 | 1.0 | 0 | 0 |
|  | 0 | 10 | 0 | 0 | 0 | 0 |
| Chlorhexidine gluconate | 1.0 | 10 | 0 | 0.5 | 32 | 32 |
|  | 1.0 | 10 | 0 | 1.0 | 33 | 32 |
|  | 1.0 | 10 | 0 | 2.0 | 34 | 32 |
|  | 1.0 | 10 | 0 | 5.0 | 34 | 32 |
|  | 1.0 | 10 | 3 | 1.0 | 35 | 31 |
|  | 1.0 | 0 | 3 | 1.0 | 34 | 31 |
|  | 1.0 | 10 | 0 | 0 | 29 | 27 |
|  | 1.0 | 10 | 3 | 0 | 0 | 0 |
|  | 0 | 10 | 3 | 1.0 | 0 | 0 |
|  | 0 | 10 | 0 | 0 | 0 | 0 |

As is apparent from Examples 1 to 6, it is understood that cationic germicides are greatly hindered in their inherent germicidal action when in the presence of an anionic surfactant and/or the like, while the germicidal action is not hindered when a metal chelating agent is added in at least preferably 0.5 mol per mol of the germicide to such a mixture. It is also understood that the compositions according to the present invention are useful compositions which satisfy both excellent germicidal power and detergency at the same time.

The present application is based on Japanese Patent Applications No.5-205076 and No.5-205077, both filed in Japan on Aug. 19, 1993, which are incorporated herein in its entirety by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A germicidal-disinfectant detergent composition comprising (a) 0.5–5 weight percent of a biguanide germicide, (b) 0.5–5 mol of a metal chelating agent per mol of the biguanide germicide, and (c) 5–50 weight percent of at least one anionic surfactant.

2. The composition according to claim 1, wherein the metal chelating agent is selected from the group consisting of ethylenediaminetetraacetic acid, hydroxyethylethylenediaminetriacetic acid, diethylenetriamine pentaacetic acid, nitrilotriacetic acid, triethylenetetramine hexaacetic acid, phosphonic acids, tripolyphosphoric acid, ethylene glycol-bis(2-aminoethyl ether)tetraacetic acid, citric acid, maleic acid, polyacrylic acid, isoamylene-maleic acid copolymers, silicic acid, gluconic acid, hydroxybenzylimidinoacetic acid, imidinoacetic acid and salts thereof.

3. The composition according to claim 1, wherein the anionic surfactant is selected from the group consisting of salts of higher fatty acids, salts of higher alcohol sulfates, salts of higher alcohol sulfonic acids, salts of sulfated fatty acids, salts of sulfonated fatty acids, salts of higher alcohol phosphates, salts of fatty acid ester sulfates, salts of fatty acid ester sulfonates, salts of higher alcohol ether sulfates, salts of higher alcohol ether sulfonates, salts of higher alcohol ether-substituted acetic acids, condensates of a fatty acid and an amino acid, salts of fatty acid amide alkylolated sulfates, salts of fatty acid amide alkylated sulfonates, salts of carboxymethyl-substituted ethoxylated fatty acid amides, salts of sulfosuccinates, alkylbenzenesulfonates, alkylphenol sulfonates, alkylnaphthalenesulfonates and alkylbenzoimidazolesulfonates.

4. The composition according to claim 1, wherein the metal chelating agent is selected from the group consisting of ethylene-diaminetetraacetic acid, hydroxyethylethylenediamine-triacetic acid, citric acid, tripolyphosphoric acid and salts thereof.

5. A method for germicidal and disinfectant cleaning, which comprises the steps of cleaning a surface with a composition comprising (a) a cationic germicide, (b) a metal chelating agent present in a proportion of at least 0.5 mol per mol of the germicide and (c) at least one surfactant selected from anionic surfactants, nonionic surfactants and amphoteric surfactants.

6. The composition as claimed in claim 1, wherein said biguanide germicide is chlorhexidine.

7. The composition as claimed in claim 1, wherein said biguanide germicide is chlorhexidine gluconate.

8. A method for germicidal and disinfectant cleaning, which comprises the step of cleaning a surface with the composition of claim 1.

9. The composition as claimed in claim 1, wherein the amount of said metal chelating agent (b) in the composition ranges from 0.5–2 mol per mol of the biguanide germicide.

10. The composition as claimed in claim 9, wherein said amount of metal chelating agent (b) ranges from 1–2 mol per mol of biguanide germicide.

* * * * *